US00PP23691P2

(12) United States Plant Patent
Ault

(10) Patent No.: US PP23,691 P2
(45) Date of Patent: Jun. 25, 2013

(54) ***ECHINACEA* PLANT NAMED 'BURGUNDY FIREWORKS'**

(50) Latin Name: ***Echinacea* hybrid**
Varietal Denomination: Burgundy Fireworks

(75) Inventor: James Robert Ault, Libertyville, IL (US)

(73) Assignee: Chicagoland Grows, Glencoe, IL (US)

( * ) Notice: Subject to any disclaimer, the term of this patent is extended or adjusted under 35 U.S.C. 154(b) by 84 days.

(21) Appl. No.: 13/200,427

(22) Filed: Sep. 23, 2011

(51) Int. Cl.
*A01H 5/00* (2006.01)

(52) U.S. Cl.
USPC ..... Plt./428

(58) Field of Classification Search
USPC ..... Plt./428
See application file for complete search history.

(56) References Cited

U.S. PATENT DOCUMENTS

PP21,771 P2 * 3/2011 Hurd ..... Plt./428
PP23,241 P2 * 12/2012 Korlipara ..... Plt./428

* cited by examiner

*Primary Examiner* — Howard Locker
(74) *Attorney, Agent, or Firm* — Penny J. Aguirre

(57) ABSTRACT

A new cultivar of hybrid *Echinacea*, 'Burgundy Fireworks', characterized by its inflorescences with ray florets that are fused their entire length into tubes or "Quills" with the trait being consistently stable throughout the inflorescence, its ray florets that are deep purplish red in color and held upwards at a 15 to 30° angle to the horizontal plane of the inflorescence, its stems that are dark purplish red in color throughout the growing season, its long bloom period, and its uniform height of about 45 cm.

2 Drawing Sheets

Botanical classification: *Echinacea* hybrid.
Variety denomination: 'Burgundy Fireworks'.

BACKGROUND OF THE INVENTION

The present invention relates to a new and distinct cultivar of hybrid *Echinacea* and will be referred to hereafter by its cultivar name, 'Burgundy Fireworks'. 'Burgundy Fireworks' represents a new purple coneflower, an herbaceous perennial grown for landscape use.

The new cultivar arose from an ongoing breeding program conducted by the Inventor in Glencoe, Ill. The breeding line was initiated in 1996 with the intent of developing a series of interspecific *Echinacea* hybrids from the species *E. purpurea, E. laevigata, E. tennesseensis*, and *E. paradoxa*. The overall objective was to develop previously unknown combinations of traits from these parents, including ornamental attributes such as unique ray floret colors, fragrance, plant bushiness, improved disease resistance, hardiness, and in-ground adaptability.

In 1996, the following four controlled crosses were made: 1) *Echinacea laevigata* hybrid×*E. purpurea* (unnamed plants), 2) *Echinacea tennesseensis*×*E. laevigata* hybrid (unnamed plants), 3) *Echinacea purpurea* 'Magnus' (not patented)×*E. tennesseensis* (unnamed plant), and 4) *Echinacea purpurea* 'Magnus'×*E. purpurea* 'Bravado' (not patented). In 1998, controlled crosses were made between the above lines 1 and 2, and between 3 and 4, and 100 and 63 plants were grown out from the two crosses, respectively. In 2000, two, plants were selected from the 1998 crosses that exhibited fused ray flowers, which had not been previously observed in this breeding program, nor reported in the literature for *Echinacea* breeding to the Inventor's knowledge. These two plants were crossed in 2000 with controlled crosses made in both directions (e.g. reciprocal cross). In 2002, six plants were selected from the reciprocal crosses made in 2000 that exhibited fused ray flowers and dark flower stems. These six plants were bulk-pollinated (e.g. pollen collected from all six plants, then hand-pollinated back on all six plants) under controlled conditions in 2002. In 2005, 'Burgundy Fireworks' was selected as a single unique plant from amongst the 100 seedlings that resulted from the 2002 crosses with the exact parent plants unknown.

Asexual propagation of the new cultivar was first accomplished by in vitro propagation of leaf petiole explants in July of 2007 by the inventor in Glencoe, Ill. and asexual propagation by in vitro propagation has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Burgundy Fireworks' as a unique cultivar of *Echinacea*.

1. 'Burgundy Fireworks' exhibits inflorescences with ray florets that are fused their entire length into tubes or "Quills" with the trait being consistently stable throughout the inflorescence.
2. 'Burgundy Fireworks' exhibits ray florets that are deep purplish red in color.
3. 'Burgundy Fireworks' exhibits ray florets that held upwards at a 15 to 30° angle to the horizontal plane of the inflorescence.
4. 'Burgundy Fireworks' exhibits sturdy stems that are dark purplish red in color throughout the growing season.
5. 'Burgundy Fireworks' exhibits a long bloom season; 12 to 14 weeks in Illinois.

6. 'Burgundy Fireworks' uniformly reaches a height of about 45 cm.

The parent plants were two of the six plants that were bulk-pollinated (e.g. pollen collected from all six plants, then hand-pollinated back on all six plants). The 6 possible parent plants differ from 'Burgundy Fireworks' in being taller in height (ranging from 61 to 91 cm), in having ray florets that are pinkish violet in color, and in having ray florets that are not consistently fused the entire length of the florets and that are not stable on all the inflorescences of the plant. 'Burgundy Fireworks' can be most closely compared to the cultivars 'All That Jazz' (U.S. Plant Pat. No. 21,771) and 'Quills and Thrills' (U.S. Plant Pat. No. 23,241). Both 'All That Jazz' and 'Quills and Thrills' are similar to 'Burgundy Fireworks' in having ray florets that are fused for some length of the ray floret and in having a long bloom season. 'All That Jazz' differs from 'Burgundy Fireworks' in having ray florets that are pinkish-lavender in color, and in being taller in height (90 cm). 'Quills and Thrills' differs from 'Burgundy Fireworks' in having ray florets that are light purple pink in color and that are fused about ⅔ of the length of the ray floret with a spoon formed at the apex.

BRIEF DESCRIPTION OF THE DRAWINGS

The accompanying photographs illustrate the overall appearance and distinct characteristics of the new cultivar. The plants in FIG. 1 and FIG. 3 were about 2 years in age as grown in a trial garden in Glencoe, Ill..

DETAILED BOTANICAL DESCRIPTION

Figure 1:
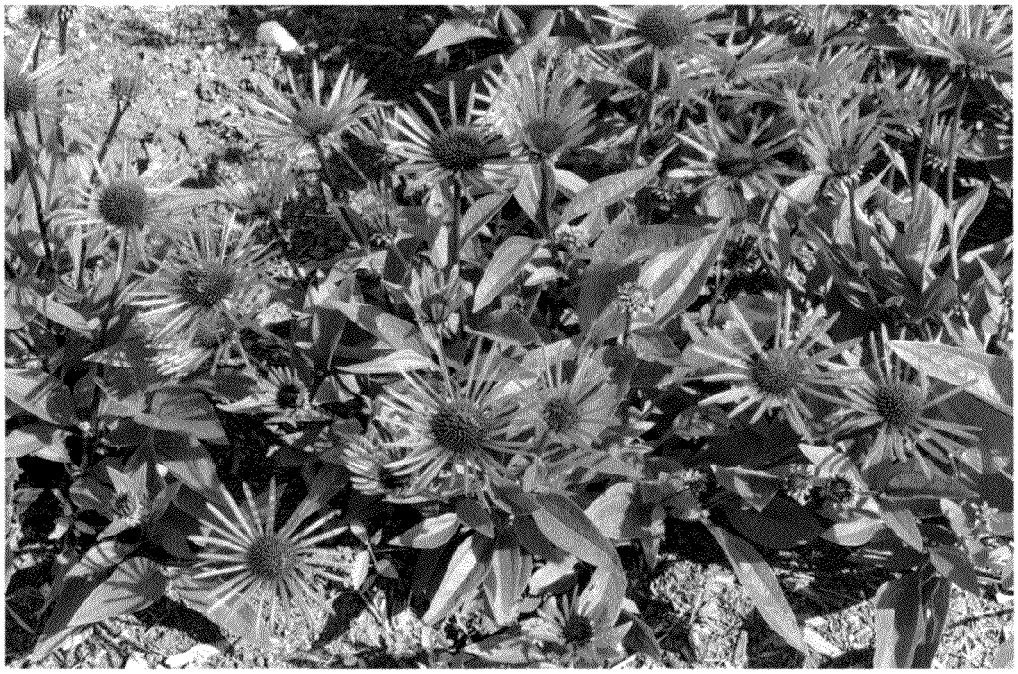
FIG. 1 provides a view of several plants of 'Burgundy Fireworks'.
Figure 2:
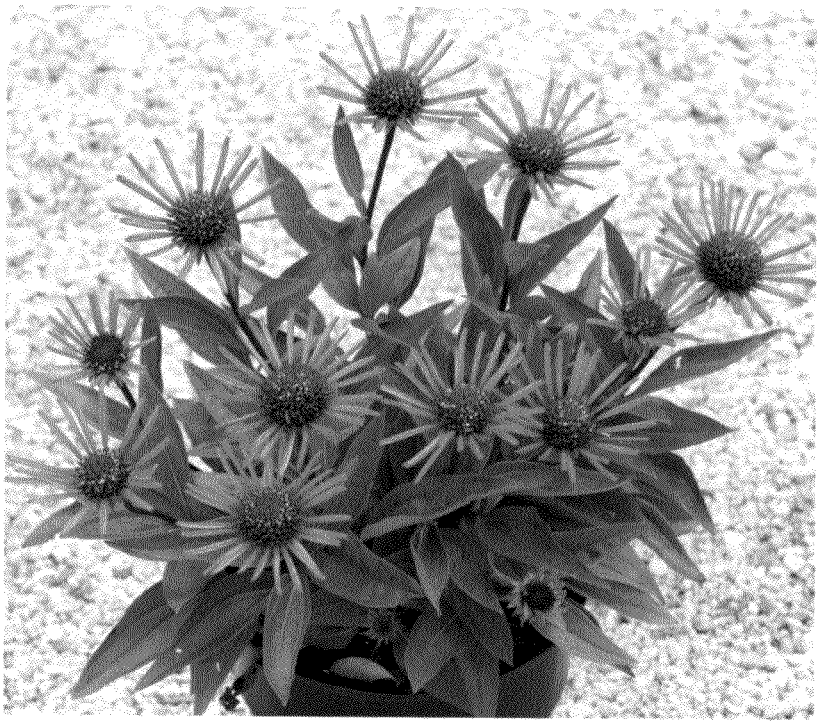
FIG. 2 provides a view of a one year-old plant of 'Burgundy Fireworks' as grown in a one-gallon container.
Figure 3:
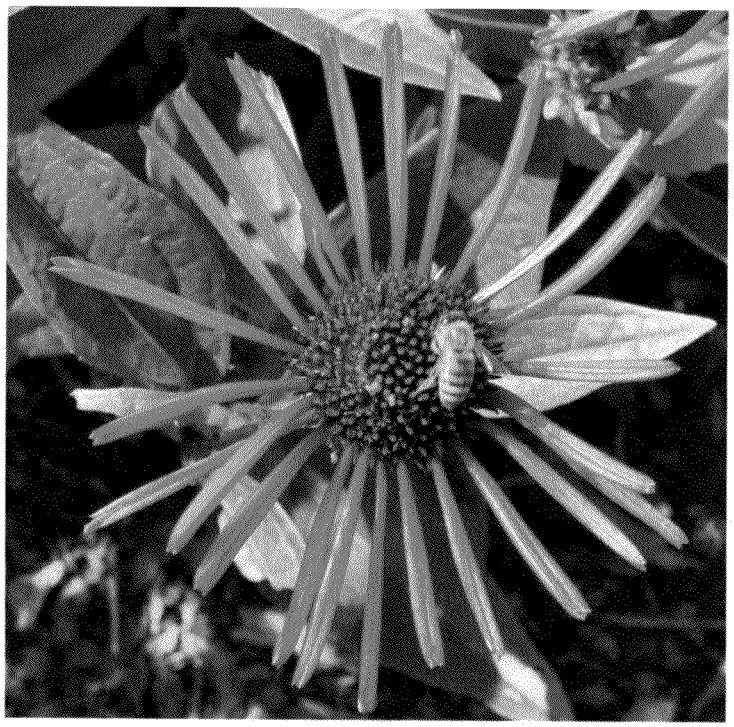
FIG. 3 provides a close-up view of an inflorescence of 'Burgundy Fireworks'. The colors in the photographs may differ slightly from the color values cited in the detailed botanical description, which accurately describe the colors of the new *Echinacea.*

The following is a detailed description of two year-old plants of the new cultivar as grown outdoors in New Hope, Minn. The phenotype of the new cultivar may vary with variations in environmental, climatic, and cultural conditions, as it has not been tested under all possible environmental conditions. The color determination is, in accordance with The 2007 R.H.S. Colour Chart of The Royal Horticultural Society, London, England, except where general color terms of ordinary dictionary significance are used.

General description:

*Blooming period.*—Blooms 12 to 14 weeks, starting in early to mid July and blooming until early to mid October in Northern Illinois.

*Plant type.*—Herbaceous perennial.

*Plant habit.*—Dwarf, compact, clump-forming, upright.

*Height and spread.*—Up to 45 cm in height and 47 cm in width (2 year-old plant).

*Hardiness.*—U.S.D.A. Zones 4 to 7.

*Diseases and pests.*—No disease or pest problems have been observed as of the date of this application, trials continue to assess any susceptibility or resistance to diseases or pests.

*Root description.*—Fibrous.

*Growth rate.*—Typical for *Echinacea.*

*Propagation.*—Tissue culture of leaf petiole explants.

Stem description:

*Shape.*—Round to oval, solid.

*Stem color.*—187A and lightly suffused with 146B, coloration is retained throughout the growing season.

*Stem size.*—Average of 4 mm in diameter and reaches an average of 30 cm in height including peduncle.

*Stem strength.*—Sturdy, even when container grown.

*Stem surface.*—Ridged, sparsely pubescent to glabrous.

*Stem number.*—An average of 12 (2 year-old plant).

Foliage description:

*Leaf shape.*—Lanceolate.

*Leaf division.*—Simple.

*Leaf base.*—Cuneate.

*Leaf apex.*—Acuminate.

*Leaf venation.*—Tri-nerved to reticulate, upper surface 144C suffused with 187B, lower surface 146C in color.

*Leaf margins.*—Entire and ciliate to minutely serrate.

*Leaf attachment.*—Petiolate.

*Leaf arrangement.*—Basal rosette and alternate on stem.

*Leaf number.*—30 to 42 basal leaves and 9 per stem.

*Internode length.*—Average of 5 cm on flowering stems.

*Leaf size.*—Up to 12 cm in length and 8 cm in width.

*Leaf color.*—Newly formed upper and lower surface; a color between 144A, mature upper; 147A, mature leaf lower surface; 137C.

*Leaf surface.*—Upper and lower surface sparsely covered with fine hairs, rough to touch, upper surface is satiny, lower surface is dull to satiny.

*Petioles.*—Extended from leaf blade, basal leaves; average of 7 cm in length and 2 cm in width, sulcate near leaf attachment, glabrous surface, 144A in color with base flushed with 187B to 187C with leafy edges 137A, stem leaves; average of 1.6 cm in length and 4 mm in width, upper surface sulcate and glabrous, 146D suffused with 187B with leafy portion 147A, lower surface 147C.

Flower description:

*Inflorescence.*—Capitulum, heterogamous with ray florets around the head margin and disk florets in the center, forming a radiant head.

*Capitulum number.*—One terminal capitulum per stem.

*Lastingness of inflorescence.*—About 4 to 6 weeks until senescence of ray flowers, disk flowers are persistent, a cut flower will last about 2 weeks.

*Capitulum size.*—Matures to about 2.5 cm in depth and 9 cm in diameter, disk size is about 2 cm in depth and 2.3 cm in diameter.

*Fragrance.*—None detected.

*Phyllaries.*—About 40 to 50 arranged in 3 overlapping rows, up to 1.5 cm in length and 4 mm in width, fused at base (truncate to stem), acuminate apex, broadly lanceolate in shape, upper and lower surfaces 146A suffused with 187A, margin entire, pubescent, combined; 3 cm in width and 1 cm in depth.

*Buds.*—Cup-shaped, up to 1.5 cm in diameter and 1 cm in depth, phyllary are 137A in color and disk flowers appear 137A with tips 200A.

*Peduncle.*—Strong, continuous with stem, 4 mm in diameter widening to about 1 cm at base of capitulum, color 187A and some suffused areas of 137C, surface sparsely pubescent.

*Ray florets (sterile).*—An average of 21 per inflorescence, florets are fused the entire length of the floret into a tube (quill), held at angle of 15 to 30° to horizontal when fully open, vertical ridges on both surfaces, about 2.5 to 3.0 cm in length and 3 to 5 mm in width, emarginated apex, truncate base, entire margin except apex, upper and lower surface glossy, color of upper and lower surface when opening; blend of 63B and 63C, color of upper and lower surface when mature 64A.

*Disk flowers* (*bisexual*).—Numerous, about 300, tubular in shape, arranged spirally on a conical receptacle, about 1 cm in length and 2 mm in width, surrounded by a palea; 1.5 cm in length and 1.5 mm in width, lanceolate in shape with an apex that terminates in a strong flexible spine, color is 144D to 144A in color with spiny apex a blend of 187A and 59A, as the floret matures the spine exceeds the length of the floret and defines the color of the disk once the reproductive organs are gone, changing from 163A to 200A as the disk florets mature and dry, corolla is comprised of 5 fused petals with acute free apex, corolla is 5 mm in length and 1.5 mm in width and N144C to N144D in color.

Reproductive organs (present on disk florets only):

*Gynoecium*.—Pistil; 1, 3 mm in length and 2 mm in width, style; 0.3 mm in width and 6 mm in length, color 145D, surrounded by stamens, stigma; bifid, villose, each arm is reflexed, about 1 mm in length and 183A in color, ovary; inferior, single-celled, 145A in color.

*Androcoecium*.—Stamens; 5, fused, form a cylinder around style, 6 mm in length, anther; 200A in color, dehisced longitudinally and 4 mm in length, filament; translucent, about 145D in color and 2 mm in length pollen; abundant and 15A in color.

*Fruit*.—Not observed; *Echinacea* is self-incompatible, fruit and seed would likely set if grown amongst other *Echinacea*.

It is claimed:

1. A new and distinct cultivar of *Echinacea* plant named 'Burgundy Fireworks' substantially as herein illustrated and described.

* * * * *